(12) United States Patent
Scott et al.

(10) Patent No.: US 8,314,594 B2
(45) Date of Patent: Nov. 20, 2012

(54) CAPACITY FADE ADJUSTED CHARGE LEVEL OR RECHARGE INTERVAL OF A RECHARGEABLE POWER SOURCE OF AN IMPLANTABLE MEDICAL DEVICE, SYSTEM AND METHOD

(75) Inventors: Erik Scott, Maple Grove, MN (US); Dave P. Guy, Maple Grove, MN (US)

(73) Assignee: Medtronic, Inc., Minneapolis, MN (US)

(*) Notice: Subject to any disclaimer, the term of this patent is extended or adjusted under 35 U.S.C. 154(b) by 1231 days.

(21) Appl. No.: 12/112,430

(22) Filed: Apr. 30, 2008

(65) Prior Publication Data
US 2009/0273313 A1    Nov. 5, 2009

(51) Int. Cl.
*H02J 7/00* (2006.01)
*G01N 27/42* (2006.01)

(52) U.S. Cl. ............................. 320/132; 324/433

(58) Field of Classification Search .......... 320/132; 324/433
See application file for complete search history.

(56) References Cited

U.S. PATENT DOCUMENTS

| | | |
|---|---|---|
| 4,949,046 A | 8/1990 | Seyfang |
| 4,952,862 A | 8/1990 | Biagetti et al. |
| 5,185,566 A | 2/1993 | Goedken et al. |
| 5,349,540 A | 9/1994 | Birkle et al. |
| 5,411,537 A | 5/1995 | Munshi et al. |
| 5,690,685 A | 11/1997 | Kroll et al. |
| 5,723,971 A | 3/1998 | Sakai et al. |
| 5,789,900 A | 8/1998 | Hasegawa et al. |
| 6,169,387 B1 | 1/2001 | Kalb |
| 6,198,253 B1 | 3/2001 | Kurle et al. |
| 6,278,258 B1 * | 8/2001 | Echarri et al. ............. 320/130 |
| 6,329,793 B1 | 12/2001 | Bertness et al. |
| 6,516,227 B1 | 2/2003 | Meadows et al. |
| 6,553,263 B1 | 4/2003 | Meadows et al. |
| 6,842,460 B1 | 1/2005 | Olkkonen et al. |
| 6,892,148 B2 * | 5/2005 | Barsoukov et al. ............ 702/63 |
| 6,928,372 B2 | 8/2005 | Pozsgay et al. |
| 7,109,684 B2 | 9/2006 | Takaoka et al. |
| 7,245,107 B2 | 7/2007 | Moore et al. |
| 7,248,929 B2 | 7/2007 | Meadows et al. |
| 7,317,947 B2 | 1/2008 | Wahlstrand et al. |
| 7,865,245 B2 | 1/2011 | Torgerson et al. |

(Continued)

FOREIGN PATENT DOCUMENTS

EP    1 048 324 A2    11/2000

(Continued)

OTHER PUBLICATIONS

International Search Report for PCT/US2009/031620.

*Primary Examiner* — Richard V Muralidar
(74) *Attorney, Agent, or Firm* — IPLM Group, P.A.

(57) ABSTRACT

System and method for estimating the time before recharging the rechargeable power source of an implantable medical device. In a method, the present charge level of the power source is determined by determining the percentage of total charge consumed over a period of time. The present charge level is then divided by the expected power use to determine time remaining before recharging. Another method utilizes a model to determine the faded capacity of the rechargeable power source based on the number of times the rechargeable power source has been charged and the duration of the rechargeable power source's life.

13 Claims, 9 Drawing Sheets

U.S. PATENT DOCUMENTS

| | | |
|---|---|---|
| 7,881,796 B2 | 2/2011 | Scott et al. |
| 2002/0140399 A1 | 10/2002 | Echarri et al. |
| 2003/0085684 A1 | 5/2003 | Tsukamoto et al. |
| 2003/0114899 A1 | 6/2003 | Woods et al. |
| 2004/0017180 A1 | 1/2004 | Cook |
| 2004/0162592 A1 | 8/2004 | Betzold et al. |
| 2004/0220758 A1 | 11/2004 | Barsoukov et al. |
| 2005/0004619 A1 | 1/2005 | Wahlstrand et al. |
| 2005/0075693 A1 | 4/2005 | Toy et al. |
| 2005/0110466 A1 | 5/2005 | Shoji et al. |
| 2005/0277994 A1 | 12/2005 | McNamee et al. |
| 2007/0063683 A1 | 3/2007 | Coq et al. |
| 2007/0069687 A1 | 3/2007 | Suzuki |
| 2007/0090790 A1 | 4/2007 | Hui |
| 2007/0156205 A1 | 7/2007 | Larson et al. |
| 2007/0257636 A1 | 11/2007 | Phillips et al. |
| 2008/0097544 A1 | 4/2008 | Gandhi et al. |
| 2008/0258679 A1 | 10/2008 | Manico et al. |
| 2009/0163820 A1 | 6/2009 | Eerden |

FOREIGN PATENT DOCUMENTS

| | | |
|---|---|---|
| EP | 1048324 | 11/2002 |
| EP | 1 610 437 A1 | 12/2005 |
| JP | 2006 046919 A | 2/2006 |
| WO | 0108749 | 2/2001 |
| WO | WO01/08749 A1 | 2/2001 |
| WO | WO01/34243 A1 | 5/2001 |
| WO | WO2008/038202 A2 | 4/2008 |

* cited by examiner

CAPACITY FADE ADJUSTED CHARGE LEVEL OR RECHARGE INTERVAL OF A RECHARGEABLE POWER SOURCE OF AN IMPLANTABLE MEDICAL DEVICE, SYSTEM AND METHOD

BACKGROUND

The medical device industry produces a wide variety of electronic devices for treating patient medical conditions using electrical stimulation. Depending upon the medical condition, medical devices can be surgically implanted or connected externally to the patient receiving treatment. Clinicians use medical devices alone or in combination with drug therapies and surgery to treat patient medical conditions. For some medical conditions, medical devices provide the best, and sometimes the only therapy to restore an individual to a more healthful condition and a fuller life. Examples of implantable medical devices designed to deliver therapeutic electrical stimulation include neurological stimulators and spinal stimulators, as well as pacemakers and defibrillators.

Because implantable medical devices provide important, oftentimes life-sustaining medical care to patients from the power supplied by a single component power source, usually a battery, the ability to know the status of that power source is critical. When a power source's charge has nearly run down, the power source must either be replaced or recharged. The failure to do so could result in the untimely failure of the implantable medical device's ability to deliver therapy to the patient, with potential consequences up to and including patient death.

A common solution to avoid having to conduct surgery to replace a depleted power source is to make the power source of the implantable medical device rechargeable via transcutaneous transmission of energy. An external power supply is operatively coupled with the rechargeable power source of the implantable medical device, often through an inductive link, and charging current is delivered to the rechargeable power source until the rechargeable power source is replenished with charge. The implantable medical device may then continue to deliver therapy to the patient until the rechargeable power source has run down again and the process of recharging may then be repeated.

SUMMARY OF THE INVENTION

However, the electrical characteristics of rechargeable batteries may tend to change either with the passage of time, with each charging and discharging cycle, or both. Among rechargeable power sources commonly in use in implantable medical devices, while the instantaneous voltage and current that may be delivered will tend to remain constant throughout the useful life of the rechargeable power source, the total amount of charge the rechargeable power source has the ability to store, i.e., the rechargeable power source capacity, may have a tendency to degrade. The tendency of the capacity of the rechargeable power source to degrade can be attributable to the effect of the passage of time, the number of charging cycles encountered, or both. The chemical nature of the rechargeable power may allow the rechargeable power source to degrade over time. Repeated charge and discharge cycles of the rechargeable power source are also known to degrade the rechargeable power source over time.

This phenomenon, known as "capacity fade", may create a challenge to the makers of implantable medical devices. If the amount of time that a rechargeable power source may provide charge is not known accurately, the rechargeable power source may run down at an unexpected and inopportune time thereby depriving potentially life-sustaining therapy to the patient.

An embodiment provides a system and method to more accurately determine how much charge remains or the recharge interval in the rechargeable power source of an implantable medical device, taking into account the capacity fade of the age of the rechargeable power source or the number of times the rechargeable power source has been charged and discharged.

An embodiment first recognizes that, although the charge capacity of a rechargeable power source has decreased, the output voltage of the rechargeable power source may tend to correspond to the same ratio of charge remaining in the rechargeable power source over the rechargeable power source's charge capacity. The implantable medical device may measure the rechargeable power source voltage at two different times and also determine the amount of charge the rechargeable power source has delivered during that time. Electronic componentry may determine the percentage of charge remaining at each of those times based on the measured rechargeable power source voltage, and subtract the second percentage from the first percentage to determine the total percentage decrease over the period of time. Then, dividing the amount of charge that was delivered between the two times by the percentage decrease of rechargeable power source charge determines the total charge capacity.

In addition, due to the nature of having an accurate picture of the charge capacity of a rechargeable power source at any given time, another embodiment more accurately determines capacity fade through means independent of the above described embodiment, perhaps to provide redundancy and improved accuracy. An embodiment may further determine capacity fade based on a model that recognizes that capacity fade occurs as a function both of the amount of time the rechargeable power source has been in use, as well as the number of times the rechargeable power source has been recharged. The charge capacity of a rechargeable power source is reduced both with the passage of time and also with use, as each charge and discharge cycle results in a decreased capacity. An embodiment utilizes a model that is unique to each type of rechargeable power supply to factor in the passage of time and the number of recharge cycles to determine the present charge capacity of a rechargeable power source at any particular time.

In an embodiment, the present invention provides a system with an implantable medical device having a rechargeable power source having a voltage, a charge level, an initial charge capacity and a present charge capacity. The system additionally has electronic componentry, operatively coupled to the implantable medical device, configured to determine a first portion of charge remaining at a first time by measuring the voltage at the first time, determine a second portion of charge remaining at a second time by measuring the voltage at the second time, the second time being different from the first time, determine a charge consumed by the implantable medical device between the first time and the second time, and determine the charge capacity by dividing the charge consumed by the difference in the second portion and the first portion.

In an embodiment, the electronic componentry is further configured to determine the charge level by multiplying the present charge capacity by the second portion.

In an embodiment, the system further comprises a charge counter, the coulomb being configured to measure the charge consumed.

In an embodiment, the electronic componentry is configured to determine the charge consumed by characterizing a power usage used by the implantable medical device.

In an embodiment, the system further comprises an external device, the external device being operatively coupled to the implantable medical device, the external device comprising the electronic componentry and a user output, the user output configured to communicate the present charge capacity to a user.

In an embodiment, the present charge capacity is a first present charge capacity, and the electronic componentry is further configured to record a cycle age by counting a number of recharges of the rechargeable power source indicative of a number of times the rechargeable power source has been recharged, record a chronological age of the rechargeable power source, determine a second present charge capacity of the rechargeable power source by subtracting a charge capacity based on the cycle age of the rechargeable power source and a charge capacity based on the chronological age of the rechargeable power source from the initial charge capacity, and determine a third present charge capacity based on the first present charge capacity and the second present charge capacity.

In an embodiment, the present invention further provides a system having an implantable medical device having a rechargeable power source having recharge interval until a recharge time when a charge level of the rechargeable power source is indicated, the rechargeable power source having an initial charge capacity, a present charge capacity and a present charge level. The system also has electronic componentry, operatively coupled to the implantable medical device, configured to record a cycle age by counting a number of recharges of the rechargeable power source indicative of a number of times the rechargeable power source has been recharged, record a chronological age of the rechargeable power source, determine the present charge capacity of the rechargeable power source by subtracting a charge capacity based on the cycle age of the rechargeable power source and a charge capacity based on the chronological age of the rechargeable power source from the initial charge capacity, measure a voltage of the rechargeable power source, determine a portion of the present charge capacity as a function of the rechargeable voltage, determine the present charge level as a function of the present charge capacity and the portion of charge capacity remaining, determine the recharge interval as a function of the present charge level and a programmed rate, and a user output, operatively coupled to the electrical componentry, configured to communicate the recharge interval to the user.

In an embodiment, the user output is further configured to communicate the present charge capacity and the initial charge capacity to the user.

In an embodiment, the electronic componentry is further configured to determine the charge capacity corresponding to the number of recharges and the charge capacity corresponding to the age of the rechargeable power source using a model.

In an embodiment, the user output is further configured to communicate a graphical depiction of the present charge capacity relative to the initial charge capacity to the user.

In an embodiment, the present invention further provides a system having an implantable medical device having a rechargeable power source, the rechargeable power source having an initial charge capacity and a present charge capacity. The system additionally has electronic componentry, operatively coupled to the implantable medical device, configured to record a cycle age by counting a number of recharges of the rechargeable power source indicative of a number of times the rechargeable power source has been recharged, record a chronological age of the rechargeable power source, determine the present charge capacity of the rechargeable power source by subtracting a charge capacity based on the cycle age of the rechargeable power source and a charge capacity based on the chronological age of the rechargeable power source from the initial charge capacity, and a user output, operatively coupled to the electronic componentry, configured to communicate the present charge capacity.

In an embodiment, the present invention further provides, in an implantable medical device having a rechargeable power source, a method for determining a present charge capacity of the rechargeable power source, the rechargeable power source having a charge level, an initial charge capacity and a voltage. The first step is determining a first portion of charge remaining at a first time by measuring the voltage at the first time. Then, a second portion of charge remaining is determined at a second time by measuring the voltage at the second time, the second time being different from the first time. A charge consumed by the implantable medical device between the first time and the second time is then determined, followed by determining the present charge capacity by dividing the charge consumed by the difference in the second portion and the first portion. A value indicative, at least in part, of the present charge capacity is then stored.

In an embodiment, the charge level is determined by multiplying the charge capacity by the second portion.

In an embodiment, the determining charged consumed step measures the charge consumed using a charge counter.

In an embodiment, the determining charge consumed step determines the charge consumed by characterizing a power usage by the implantable medical device.

In an embodiment, the method also has the step of outputting the charge capacity to a user.

In an embodiment, the present charge capacity is a first present charge capacity, and the method further also includes recording a cycle age by counting a number of recharges of the rechargeable power source indicative of a number of times the rechargeable power source has been recharged. Then a chronological age of the rechargeable power source is recorded, and a second present charge capacity of the rechargeable power source is determined by subtracting a charge capacity based on the cycle age of the rechargeable power source and a charge capacity based on the chronological age of the rechargeable power source from the initial charge capacity. Then an average present charge capacity is determined by averaging the first present charge capacity and the second present charge capacity, and a value indicative, at least in part, of the average present charge capacity is stored.

In an embodiment, the present invention further provides, in an implantable medical device having a rechargeable power source, a method for determining a recharge interval until a recharge time when a charge level of the rechargeable power source reaches a value at which recharging of the rechargeable power source is indicated, the rechargeable power source having an initial charge capacity, a present charge capacity and a present charge level. First, a cycle age is recorded by counting a number of recharges of the rechargeable power source indicative of a number of times the rechargeable power source has been recharged. Then a chronological age of the rechargeable power source is recorded. The present charge capacity of the rechargeable power source is determined by subtracting a charge capacity based on the cycle age of the rechargeable power source and a charge capacity based on the chronological age of the rechargeable power source from the initial charge capacity, measuring a voltage of the rechargeable power source, determining a portion of the present charge capacity as a function of the rechargeable voltage, finally determining the present charge level as a function of the present charge capacity and the portion of charge capacity remaining. The recharge interval is determined as a function of the present charge level and a programmed rate, and outputted to a user.

In an embodiment, the present charge capacity and the initial charge capacity is outputted to the user.

In an embodiment, the charge capacity corresponding to the number of recharges and the charge capacity corresponding to the age of the rechargeable power source are determined using a model.

In an embodiment, the outputting step outputs a graphical depiction of the present charge capacity relative to the initial charge capacity.

In an embodiment, the rechargeable power source has a voltage and the present charge capacity is a first present charge capacity. Then a first portion of charge remaining at a first time by measuring the voltage at the first time is determined. A second portion of charge remaining at a second time by measuring the voltage at the second time is then determined, the second time being different from the first time, followed by the determination of a charge consumed by the implantable medical device between the first time and the second time. The second present charge capacity is determined by dividing the charge consumed by the difference in the second portion and the first portion, as is the second present charge level as a function of the second present charge capacity and the second portion. Finally, the recharge interval is determined as a function of the first present charge level and the second present charge level.

In an embodiment, the present invention further provides, in an implantable medical device having a rechargeable power source, a method for determining a present charge capacity of the rechargeable power source, the rechargeable power source having an initial charge capacity. A cycle age is recorded by counting a number of recharges of the rechargeable power source indicative of a number of times the rechargeable power source has been recharged, and then a chronological age of the rechargeable power source is recorded. Then the present charge capacity of the rechargeable power source is determined by subtracting a charge capacity based on the cycle age of the rechargeable power source and a charge capacity based on the chronological age of the rechargeable power source from the initial charge capacity. Finally, the present charge capacity and the initial charge capacity are outputted to a user.

In an embodiment, the charge capacity corresponding to the number of recharges and the charge capacity corresponding to the age of the rechargeable power source are determined using a model.

In an embodiment, the outputting step outputs a graphical depiction of the present charge capacity relative to the initial charge capacity.

In an embodiment, the rechargeable power source has a voltage and the present charge capacity is a first present charge capacity. A first portion of charge remaining at a first time is determined by measuring the voltage at the first time, and a second portion of charge remaining at a second time is determined by measuring the voltage at the second time, the second time being different from the first time. A charge consumed by the implantable medical device between the first time and the second time is then determined, as is the second present charge capacity by dividing the charge consumed by the difference in the second portion and the first portion. A third present charge capacity is determined as a function of the first charge capacity and the second charge capacity, and the third present charge capacity is output to a user.

DRAWINGS

DESCRIPTION

Figure 1:
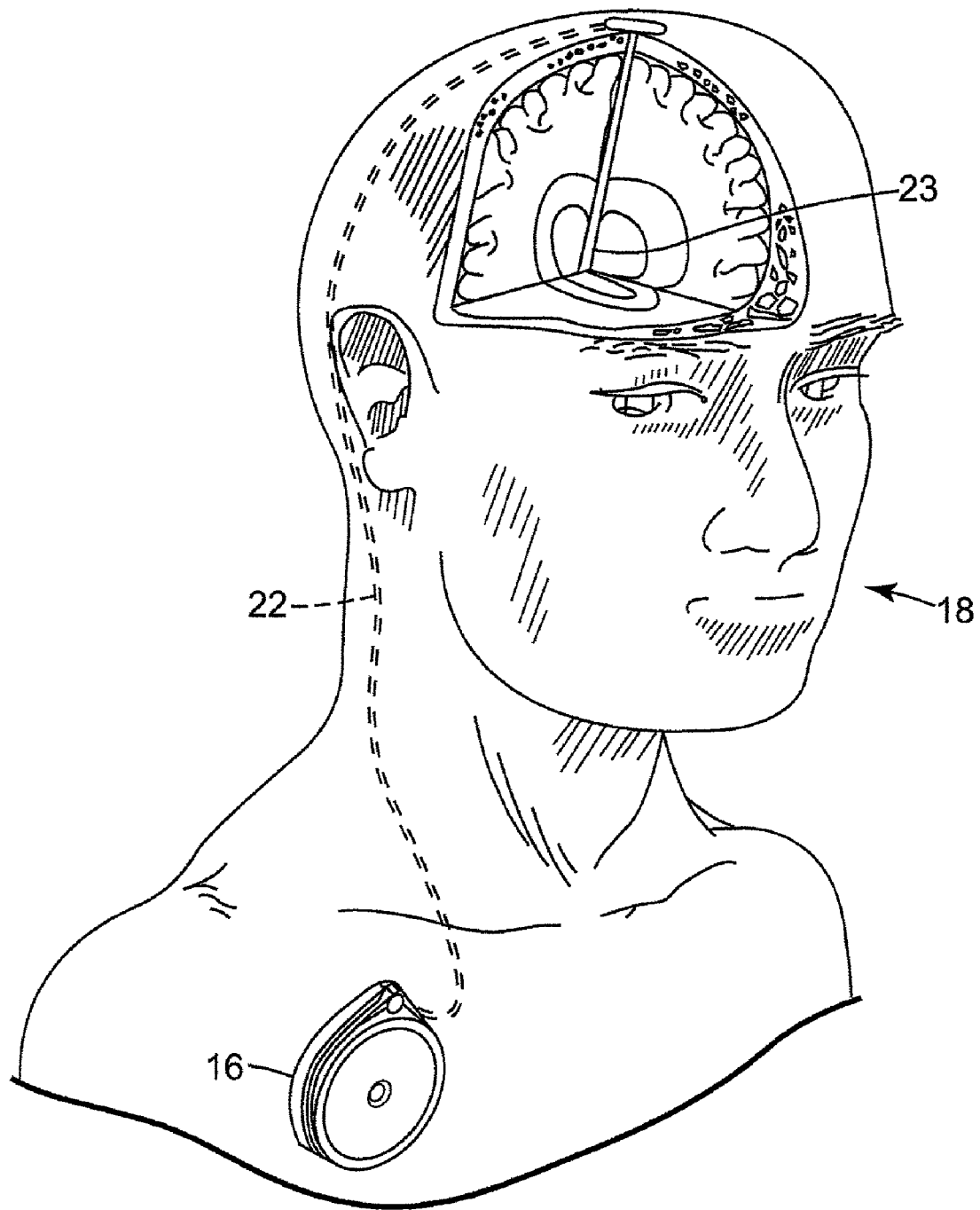
FIG. 1 shows an implantable medical device implanted in a patient.

The charge capacity of a rechargeable power source can tend to decline or "fade" over time. This phenomenon can be due to a variety of factors. In Lithium-Ion batteries, fade can be traceable to issues of the growth of solid-electrolyte interfaces in lithium-ion cells incorporating carbon anodes. It can also be a result of lithium-ion molecule isolation as a result of chemical changes in the rechargeable power source, as well as the sequestering of lithium molecules. Host material degradation may also play a role, as the phase change of individual molecules, the isolation and fracture of elements of the rechargeable power source and blocked sites all reduce locations of accessible charge. Increased resistance in the rechargeable power source material tends to reduce the efficiency of charge transfer, reducing the charge that can be drawn from the rechargeable power source. Examples of increased resistance include particle-to-particle resistance within the rechargeable power source, separator resistance, as well as charge-transfer resistance out of the cell. Parasitic reactions occurring within the rechargeable power source cell may also degrade the charge capacity, such as reactions from electrolytes and solvents that may tend to be present in the rechargeable power source cell, reactions from industrial additives and impurities in the chemical compound to of the rechargeable power source.

A rechargeable power source has a charge capacity or total charge capacity, i.e., the maximum amount of charge that a rechargeable power source is capable of storing at any particular point in time. The total charge capacity is a function of the age of the rechargeable power and, typically, degrades over time and/or over charge cycles. Total charge capacity is typically measured in ampere-hours, milliampere-hours, watt-hours or similar units.

A charge level of a rechargeable power source is the amount of energy or amount of charge actually stored in the rechargeable power at a particular point in time. Charge level is typically measured in ampere-hours, watt-hours, coulombs or similar units.

The net charge of a rechargeable power source is similar to the charge level and represents the energy, typically in coulombs, actually stored in the rechargeable power source.

The state of charge of a rechargeable power source is a fractional unit between zero and one representing the portion of the net charge stored in the rechargeable power source relative to the total charge capacity of the rechargeable battery. The state of charge is typically measured or represented by a fraction, decimal or percentage value.

The first state of charge of a rechargeable power source is a state of charge of the rechargeable measured or represented at a first point in time, e.g., the state of charge existing in the rechargeable power source at a point in time when recharging of the rechargeable power source is commenced.

The net charge remaining or charge remaining in a rechargeable power source is a function of the total charge capacity multiplied by the state of charge:

$$Q_{remaining} = Q_{total} * (SOC).$$

This relationship can be expressed conversely during charging of the rechargeable power source in that the net charge remaining is a function of the total charge capacity times the state of charge subtracted from one:

$$Q_{remaining} = Q_{total} * (1 - SOC).$$

The state of charge of a rechargeable power source can be assessed by, for example, either (A) measuring the voltage, e.g., of a cell, and comparing the voltage measured to a standard curve of voltage versus state of charge of a particular type or particular one of a rechargeable power source; or (B) measuring the amount of charge, e.g., coulombs, delivered by the rechargeable power source; or some combination of the two methods.

Prediction of the total charge capacity of the rechargeable power source (Qtotal) may be assessed either by (A) knowledge of the initial charge capacity, perhaps with appropriate correction due to fade, e.g., battery fade, that may account for the number of charge cycles and age of the rechargeable power source; or (B) assessing the state of charge of the rechargeable power source at two or more points, as well as the measured amount of charge delivered by the rechargeable power source between the same two points ($Q_{measured}$), according to the relationship:

$$Q_{total} = Q_{measured} / \Delta SOC.$$

An alternative way to assess the total charge capacity ($Q_{total}$) is from a capacity fade model, for example:

$$Q_{total} = Q_{total}(\text{initial}) - \Delta Q(\text{time}) - \Delta Q(\text{cycles}),$$

wherein $\Delta Q$(cycles) is generally a linear function of the number of cycles and $\Delta Q$(time) is a linear or exponential decay function over time.

The amount of time remaining before a rechargeable power source needs to be recharged or until a charge cycle is complete, along a measured or estimated value of average current drain, can be shown in the relationship:

$$t_{remaining} = Q_{remaining} / \text{current}.$$

The foregoing basic relationships form a foundation for the following description.

An embodiment relies on the determined fact that while the charge capacity of a rechargeable power source may decrease or fade, the voltage output from the rechargeable power source tends nevertheless to continue to correspond to a particular percentage of the charge capacity of the rechargeable power source at a given point in time. Thus, voltage level V1 will tend to correspond to the percentage of the total charge capacity at a first time P1, regardless of what the total charge capacity of rechargeable power happens to be at any given moment. However, without knowing what the total charge capacity is, knowing P1 does not inform a user how much charge is actually remaining in the rechargeable power source. To determine this, a percentage of total charge capacity at a second, initial time P2 is determined and that percentage is used with P1 to determine both the total charge capacity and the charge level.

A system with an implantable medical device having a rechargeable power source subject to capacity fade is depicted generically in FIG. 1, which shows implantable medical device 16, for example, a neurological stimulator, implanted in patient 18. The implantable medical device 16 is typically implanted by a surgeon in a sterile surgical procedure performed under local, regional, or general anesthesia. Before implanting the medical device 16, a lead 22 is typically implanted with the distal end position at a desired therapeutic delivery site 23 and the proximal end tunneled under the skin to the location where the medical device 16 is to be implanted. Implantable medical device 16 is generally implanted subcutaneously at depths, depending upon application and device 16, of from 1 centimeter (0.4 inches) to 2.5 centimeters (1 inch) where there is sufficient tissue to support the implanted system. Once medical device 16 is implanted into the patient 18, the incision can be sutured closed and medical device 16 can begin operation.

Implantable medical device 16 can be any of a number of medical devices such as an implantable therapeutic substance delivery device, implantable drug pump, electrical stimulator, cardiac pacemaker, cardioverter or defibrillator, as examples.

If implantable medical device 16 is a drug infusion device, for example, implantable medical device 16 operates to infuse a therapeutic substance into patient 18. Implantable medical device 16 can be used for a wide variety of therapies such as pain, spasticity, cancer, and many other medical conditions.

The therapeutic substance contained in implantable medical device 16 is a substance intended to have a therapeutic effect such as pharmaceutical compositions, genetic materials, biologics, and other substances. Pharmaceutical compositions are chemical formulations intended to have a therapeutic effect such as intrathecal antispasmodics, pain medications, chemotherapeutic agents, and the like. Pharmaceutical compositions are often configured to function in an implanted environment with characteristics such as stability at body temperature to retain therapeutic qualities, concentration to reduce the frequency of replenishment, and the like. Genetic materials are substances intended to have a direct or indirect genetic therapeutic effect such as genetic vectors, genetic regulator elements, genetic structural elements, DNA, and the like. Biologics are substances that are living matter or derived from living matter intended to have a therapeutic effect such as stem cells, platelets, hormones, biologically produced chemicals, and the like. Other substances may or may not be intended to have a therapeutic effect and are not easily classified such as saline solution, fluoroscopy agents, disease diagnostic agents and the like. Unless otherwise noted in the following paragraphs, a drug is synonymous with any therapeutic, diagnostic, or other substance that is delivered by the implantable infusion device.

If implantable medical device 16 is an electrical stimulator, for example, therapy module 28 may deliver an electrical stimulus, such as an electrical pulse, or series of electrical pulses, either mono-polar or bi-polar, through one or more electrical leads and/or electrodes to provide specific or general benefit to that patient such as pain relief or muscular control.

Figure 2:
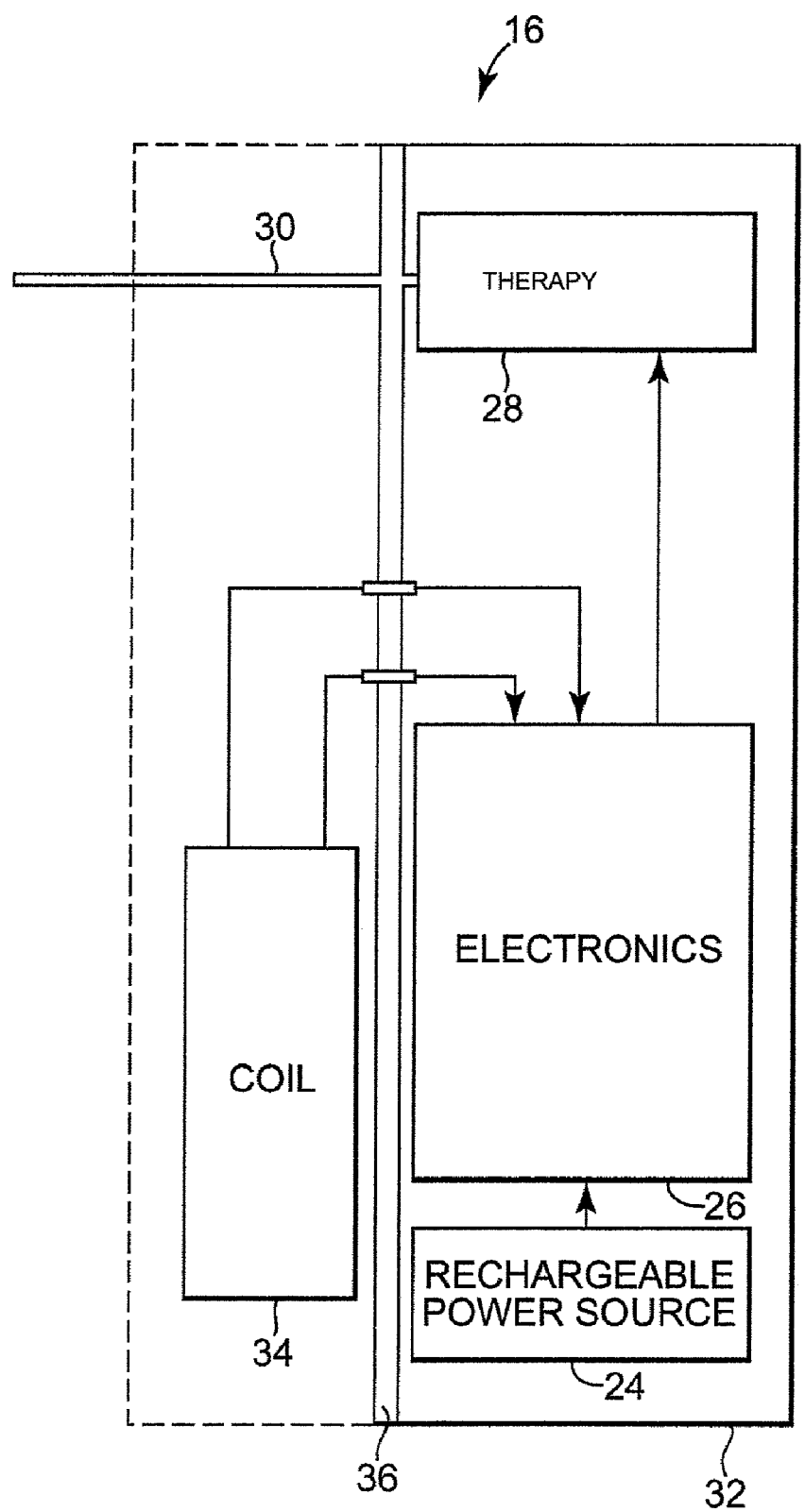
FIG. 2 shows a block diagram of an implantable medical device.

In FIG. 2, implantable medical device 16 has a rechargeable power source 24, such as a Lithium ion battery, powering electronic componentry, such as electronics 26 and therapy module 28 in a conventional manner. Therapy module 28 is coupled to patient 18 through one or more therapy connections 30, also conventionally. Rechargeable power source 24, electronics 26 and therapy module 28 are contained in hermetically sealed housing 32. Secondary charging coil 34 may be interior to housing 32 or attached to the exterior of housing 32. Secondary charging coil 34 is operatively coupled through electronics 26 to rechargeable power source 24. In an alternative embodiment, secondary charging coil 34 could be contained in housing 32 or could be contained in a separate housing umbilically connected to electronics 26. Electronics 26 help provide control of the charging rate of rechargeable power source 24 in a conventional manner. Magnetic shield 36 is positioned between secondary charging coil 34 and housing 32 in order to protect rechargeable power source 24, electronics 26 and therapy module 28 from electromagnetic energy when secondary charging coil 34 is utilized to charge rechargeable power source 24.

Rechargeable power source 24 can be any of a variety power sources including a chemically based battery or a capacitor. Rechargeable power source may be a well known lithium ion battery.

Figure 3:
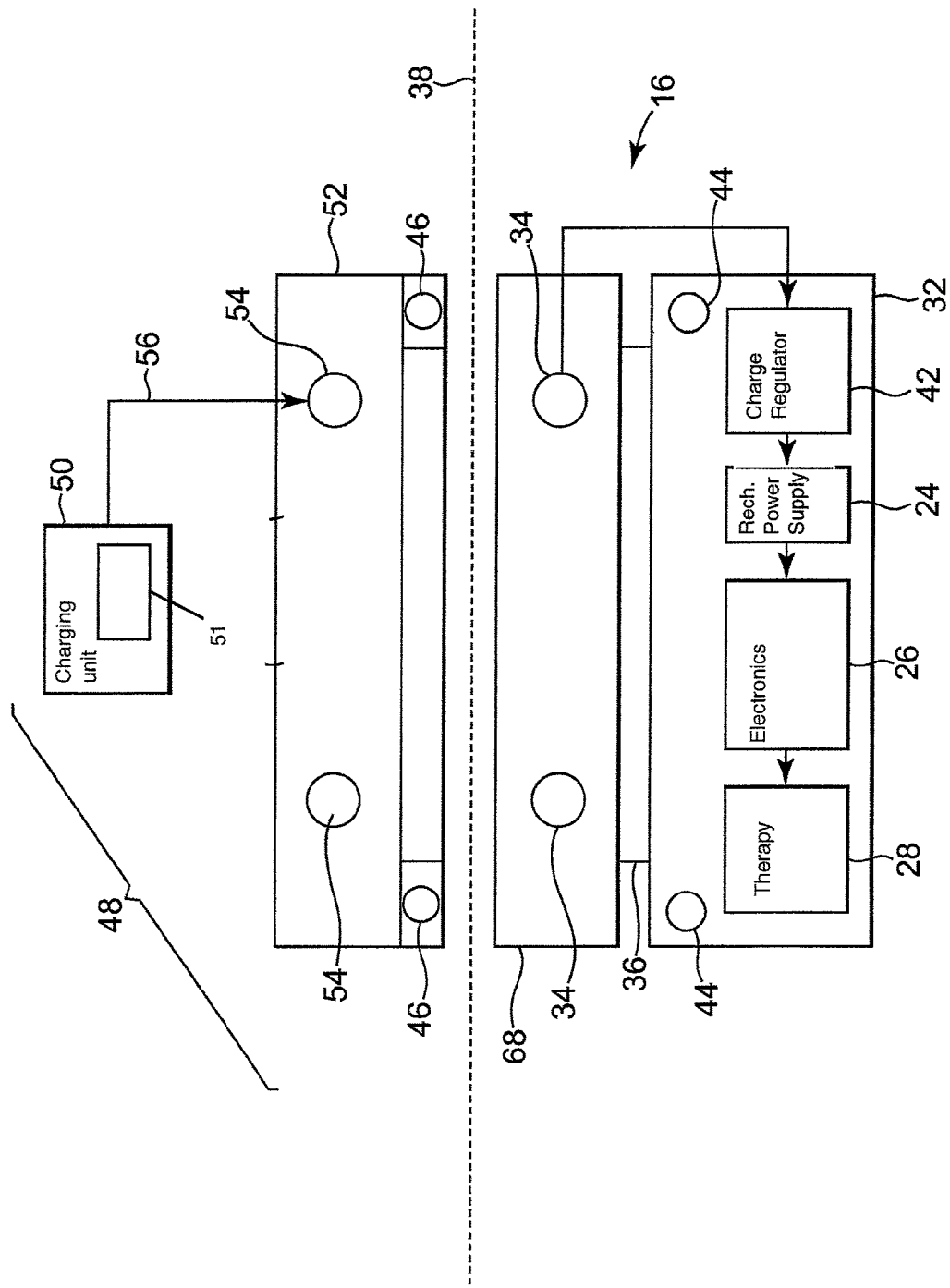
FIG. 3 shows an expanded block diagram of an implantable medical device, and an external charger.

FIG. 3 illustrates an alternative embodiment of implantable medical device 16 situated under cutaneous boundary 38. Implantable medical device 16 is similar to the embodiment illustrated in FIG. 2. However, charging regulation module 42 is shown separate from electronics 26 controlling therapy module 28. Again, charging regulation and therapy control is conventional. Implantable medical device 16 also has internal telemetry coil 44 configured in conventional manner to communicate through external telemetry coil 46 to an external programming device (not shown), charging unit 50 or other device in a conventional manner in order to both program and control implantable medical device 16 and to externally obtain information from implantable medical device 16 once implantable medical device 16 has been implanted. Internal telemetry coil 44, rectangular in shape with dimensions of 1.85 inches (4.7 centimeters) by 1.89 inches (4.8 centimeters) constructed from 150 turns of 43 AWG wire, is sized to be larger than the diameter of secondary charging coil 34 in internal antenna 68. Secondary coil 34 is constructed with 182 turns of 30 AWG wire with an inside diameter of 0.72 inches (1.83 centimeters) and an outside diameter of 1.43 inches (3.63 centimeters) with a height of 0.075 inches (0.19 centimeters). Magnetic shield 36 is positioned between secondary charging coil 34 and housing 32 and sized to cover the footprint of secondary charging coil 34.

Internal telemetry coil 44, having a larger diameter than secondary coil 34, is not completely covered by magnetic shield 36 allowing implantable medical device 16 to communicate with the external programming device with internal telemetry coil 44 in spite of the presence of magnetic shield 36.

Rechargeable power source 24 can be charged while implantable medical device 16 is in place in a patient through the use of external charging device 48. In an embodiment, external charging device 48 consists of charging unit 50 and external antenna 52. Charging unit 50 may contain electronic componentry, which may include the electronics necessary to drive primary coil 54 with an oscillating current in order to induce current in secondary coil 34 when primary coil 54 is placed in the proximity of secondary coil 34. Charging unit 50 is operatively coupled to primary coil by cable 56. In an alternative embodiment, charging unit 50 and antenna 52 may be combined into a single unit. Antenna 52 may also optionally contain external telemetry coil 46 which may be operatively coupled to charging unit 50 if it is desired to communicate to or from implantable medical device 16 with external charging device 48. Alternatively, antenna 52 may optionally contain external telemetry coil 46 which can be operatively coupled to an external programming device, either individually or together with external charging unit 48.

Charging unit 50 may further include a user output 51, such as a display or a means for producing an audio output, for transmitting information to a user. Such a user output 51 may also be included in a patient programmer, a physician programmer, or any device operably coupled to implantable medical device 16 or charging unit 50.

Figure 4:
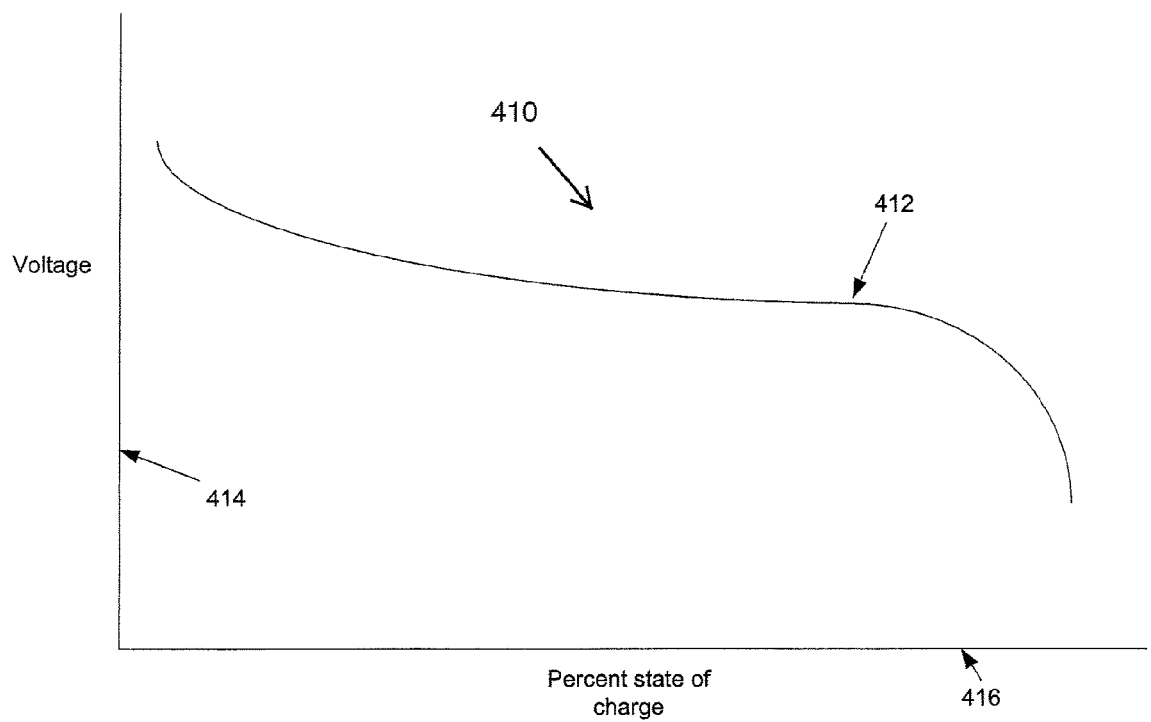
FIG. 4 shows a graphical depiction of a model of charge level of a power source relative to output voltage.

FIG. 4 is a graphical depiction of model 410 of the relationship of voltage output 414 of rechargeable power source 24 to percentage of charge remaining 416 or "charge level" in rechargeable power source 24 to the total charge capacity of rechargeable power source 24. Regardless of the total charge capacity of rechargeable power source 24, a particular voltage output will correspond to the same percentage of charge level over total charge capacity, depicted by curve 412. In an embodiment, where the charge level equals the total charge capacity, output voltage will be approximately 4.0 volts. In an example, it may be desired that the voltage output stay above approximately 3.5 volts for rechargeable power source 24 to be able to continue to supply implantable medical device 16 with suitable power.

Figure 5:
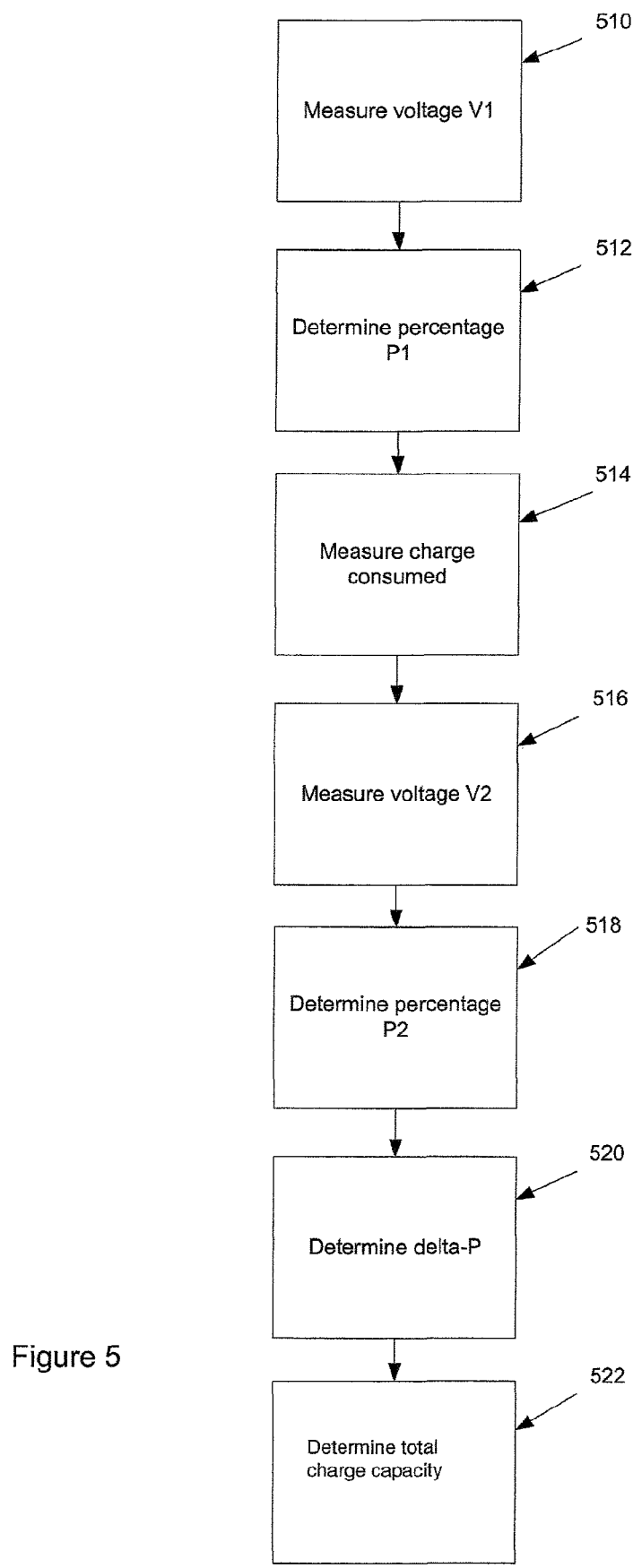
FIG. 5 is a flow chart of a method for determining the total charge capacity of a rechargeable power source.

FIG. 5 illustrates a flow chart for determining the total charge capacity of rechargeable power source 24 in electronic componentry that may be included in implantable medical device 16, charging unit 50, a patient programmer, a physician programmer, or other devices that may be operably coupled to implantable medical device 16. During normal use of implantable medical device 16, the voltage output V1 of rechargeable power source 24 is measured (510) and recorded in electronics 26. V1 is transmitted to external charging device 48, which determines (512) a percentage of charge remaining P1 by referencing model 410. In an alternative embodiment, P1 is determined (512) and stored in electronics 26. After some period of time during which implantable medical device 16 functions normally, monitoring and delivering therapy, electronics 26 determines (514) the net charge passed through rechargeable power source 24 or consumed by implantable medical device 16. This can be accomplished in a number of ways, including using a coulomb counter operatively coupled to rechargeable power source 24, using a current meter operatively coupled to rechargeable power source 24, or by characterizing the power consumption of the individual components of implantable medical device 16, and determining the amount of charge consumed based on those characteristics and device settings. At the end of the period of time, voltage output V2 of rechargeable power source 24 is measured (516) and stored, and percentage P2 is determined (518) in the same manner as P1.

Percentage P2 is then subtracted from P1 in order to determine (520) the change in percentage of charge level over the period of time, delta-P. The charge consumed is then divided by delta-P to determine (522) the total charge capacity of rechargeable power source 24. In various embodiments, these calculations may occur either in electronics 26 of implantable medical device 16, or in external charging unit 48. Once total charge capacity has been determined, a following step of multiplying P2 by the total charge capacity may be performed to determine the present charge level, which may be outputted to a user. This further step may make the data more useful to more users by determining a time remaining until recharge by dividing the present charge level by an expected charge consumption (see FIG. 6).

In an embodiment, as part of determining the present charge level (see FIG. 5) the amount of charge delivered by rechargeable power source 24 was determined (514). In a further embodiment, that determined charge consumption may be utilized to determine how long, given the present charge level, the charge in rechargeable power source 24 may likely last until implantable medical device 16 indicates a recharge session is needed. By dividing the present charge level by the amount of charge consumed, adjusted for the amount of time over which the charge consumed was determined, an estimate of the amount of time remaining on the present charge level may be determined. In an alternative embodiment, the charge consumption variable may not be the determined value from (514), but rather from a longer-term determination of the amount of charge consumed per unit time, acquired in the same manner as the determination from (514), only over a longer period of time. The alternative embodiment may carry the advantage of utilizing an average power consumption less-prone to short term variances in the amount of charge consumption than that utilized in FIG. 5, while potentially carrying the disadvantage of being less-representative of the current nature of the utilization of the charge in rechargeable power source 24. Which of the possible embodiments may best serve to predict future performance is a determination that may be dependent on the tendencies of individual patients 18 and characteristics of individual implantable medical devices 16.

Figure 6:
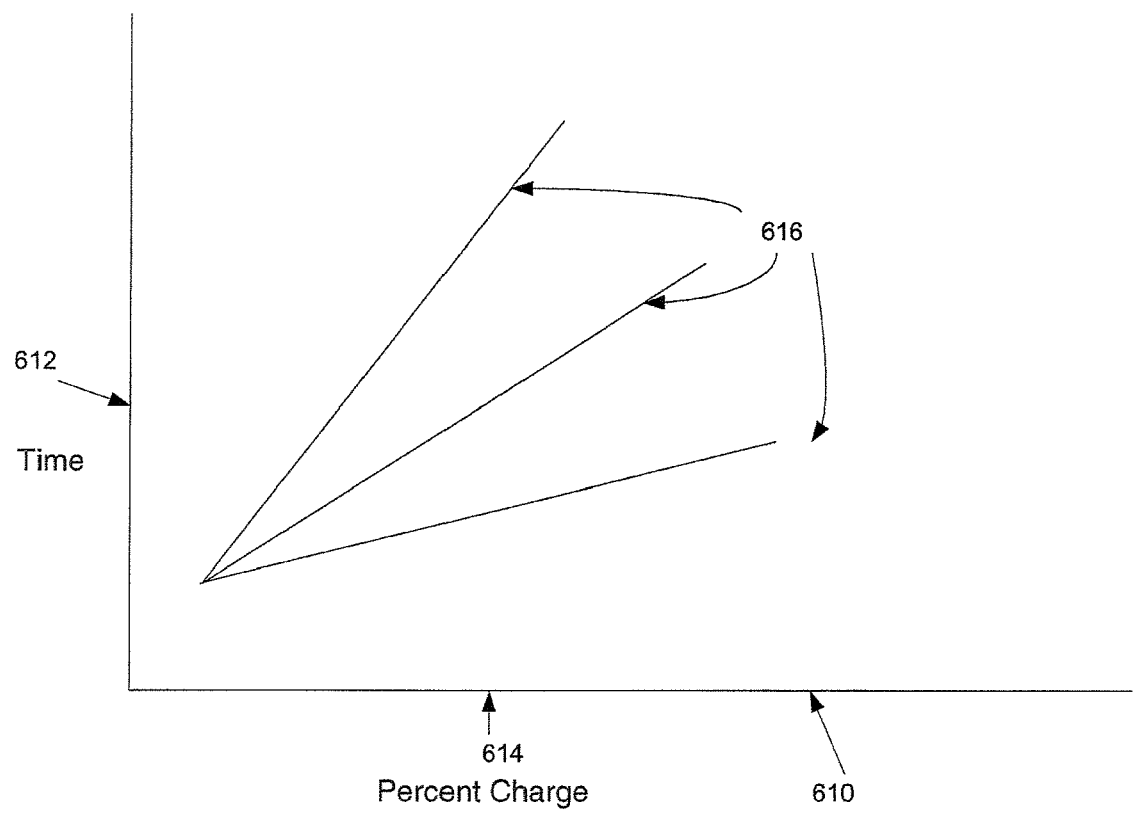
FIG. 6 shows a graphical representation of the impact on the time until recharge based on the percentage of charge in rechargeable power source and the anticipated rate of power consumption.

FIG. 6 shows a graphical representation 610 of the impact on the time until recharge 612 based on the percentage of charge in rechargeable power source 614 and the anticipated rate of power consumption 616, represented by a plurality of curves 616 representative of the possible amount of current consumption. Where the percentage charge remaining is low, then the amount of charge consumption may ultimately have minimal impact on the amount of time before recharging is indicated. By contrast, where the percentage of charge remaining is relatively high, the amount of charge consumption can have a significant impact on the amount of time remaining.

Figure 7:
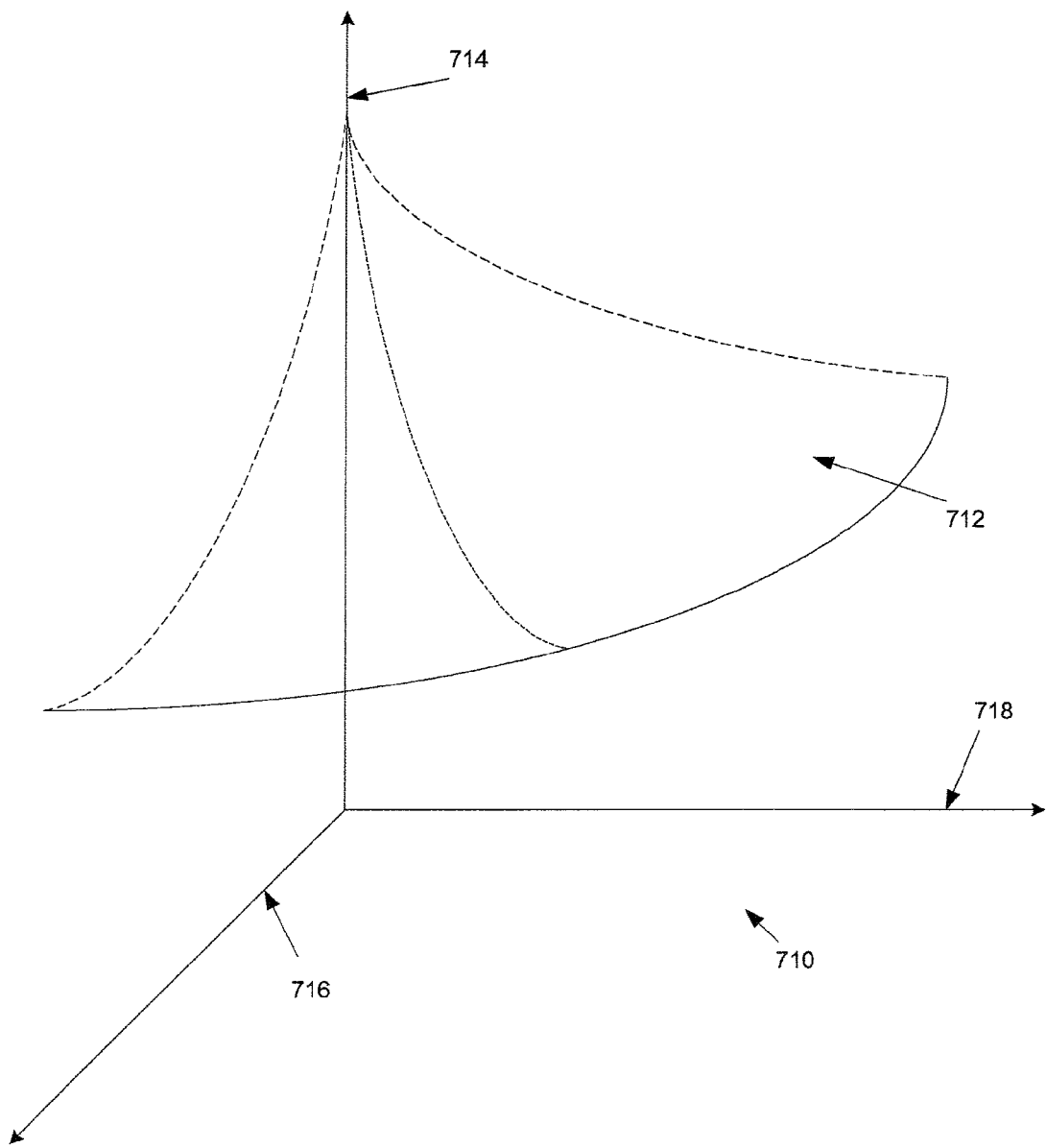
FIG. 7 shows a graphical depiction of a model of the relationship of total charge capacity as a function of time and recharge cycles.

FIG. 7 is a graphical depiction of model 710 of the relationship of total charge capacity as a function of time and recharge cycles. Surface 712 represents the charge capacity of rechargeable power supply, represented on Z-axis 714, based on the amount of time rechargeable power source 24 has been in operation, in other words a chronological age of rechargeable power source 24, represented on Y-axis 716, and the number of charge and discharge cycles rechargeable power source 24 has experienced, in other words, representative of a cycle age of rechargeable power source 24, represented on X-axis 718. Thus, for any two values of cycles and time, the charge capacity of rechargeable power source may be determined by referencing the corresponding location on surface 712.

The impact of time on capacity fade is determined by a number of factors, each of which are dependent on the particular rechargeable power supply 24 in question. Factors such as the chemistry of rechargeable power source 24, temperature and voltage output affect the impact of time on rechargeable power source 24. For instance, certain materials used in rechargeable power sources 24 may tend to degrade through parasitic reactions at a greater rate than other materials. Likewise, rechargeable power sources 24 operating at high temperatures may tend to degrade faster than rechargeable power sources 24 operating at low temperatures. Finally, a rechargeable power source 24 that operates at a relatively high voltage may naturally tend to deplete its charge faster than a rechargeable power source 24 that operates at a relatively lower voltage. These factors all tend to be independent of actually recharging rechargeable power source and may tend to occur with any battery or other similar rechargeable power source. In various embodiments, the impact of time on capacity fade may be an exponential decay with the passage of time, with the passage of time having a greater impact on capacity fade toward the end of rechargeable power source's 24 life than at the beginning.

The impact of recharge cycles on capacity fade is likewise dependent on several factors. The mechanical design of rechargeable power source 24 may impact how the inflow and outflow of charge impacts the ability to take and deliver charge. Where rechargeable power source 24 is comprised of a plurality of cells, balance between and among the various cells may have an impact on capacity after repeated recharge cycles. Voltage limits likewise may have an impact, as extreme voltages, either high or low, may impact capacity fade. The rate of the inflow of charge into rechargeable power source 24 may also tend to impact the charge capacity of rechargeable power source 24. In various embodiments, the number of recharge cycles may have a linear relationship on capacity fade, with each recharge cycle reducing the total capacity by an amount approximately equal to that caused by every other recharge cycle.

In various embodiments, the impact of a recharge cycle on capacity fade may be reduced if rechargeable power source has not been charged from having essentially no charge to being essentially full to the total charge capacity. For instance, in an embodiment, a recharge cycle that takes the charge level of rechargeable power source 24 from 25% of total charge capacity to 75% of total charge capacity may result in only half the capacity fade as if the recharge cycle took the charge level from approximately 0% to approximately 100%. In such an embodiment, the relationship between the percentage change of charge level to total charge capacity may be linear with respect to capacity fade. In alternative embodiments, the relationship may not be linear, with capacity fade rather being dependent on a combination of, first, whether a recharge cycle of any kind has occurred, and, second, the amount of charge transferred. Thus, in an embodiment, a recharge cycle that takes the charge level of rechargeable power source 24 from 25% of total charge capacity to 75% of total charge capacity may result in three-quarters of the capacity fade as if the recharge cycle took the charge level from approximately 0% to approximately 100%.

Various alternative embodiments with alternative characteristics are possible and may be dependent on the physical characteristics of rechargeable power source 24. For instance, a particular percentage increase in charge level relative to total charge capacity may result in a different impact on capacity fade than a different percentage increase in charge level depending on the starting charge level and ending charge level as a percentage of total charge capacity. In such an embodiment, there may be a greater impact on capacity fade if the starting charge level is relatively closer to 0% of total charge capacity or the ending charge level is relatively closer to 100% of total charge capacity.

In order to determine total charge capacity of rechargeable power source 24 (FIG. 8), electronics 26 determine if a recharge cycle has occurred (810), and if so, increment (812) a counter in electronics 26 tracking the number of recharge sessions that have occurred. In an embodiment, the counter is incremented by one with each recharge session. In an alternative embodiment, the counter is incremented based on a proportion of the total charge capacity the charge level of rechargeable power source was increased. Electronics 26 likewise updates and records (814) the amount of time since rechargeable power source has been active. When prompted by a user, it is determined (816) what the total charge capacity of rechargeable power source 24 is based on the total charge capacity at the initial time of rechargeable power source 24, the recorded time, and the recorded number of cycles, using the model depicted graphically in FIG. 7. In an embodiment, this determination is made in electronics 26. In an alternative embodiment, this determination is made in external charging device 48 after the data on total charge capacity at the second, initial time, recorded time and recorded number of cycles has been transmitted to external charging device 48. If determination (816) was conducted in implantable medical device 16, the result is transmitted to external charging device 48 and outputted (818) to a user. Alternatively, if determination (816) was conducted in external charging device 48 it is simply outputted (818) to a user. In an embodiment, the total charge capacity is outputted to a user via an external device other than external charging unit 48, such as a physician programmer or a patient programmer. Communication may be by telemetry, passive telemetry, radio frequency (RF), induction, ultrasound, audible sound, optics or other communication techniques. State of charge may be represented, for example, by a bar graph.

Commonly, a user may desire further information beyond the total charge capacity. In an embodiment (FIG. 8), the total charge capacity is used to determine other information to provide to a user. In an embodiment, total charge capacity is outputted to a user via external charging device 48 along with the total charge capacity at the initial time, comparing the two values in graphical form (see FIG. 9). One example would be as a gas gauge, with the total charge capacity at the initial time representing the total area of the gauge, and the total are being divided into total charge capacity and lost charge capacity. While a pie chart is illustrated, other forms are possible, such as status bars, lines, grids, and other forms commonly known in the art. This information will allow a medical professional to make an accurate assessment of the degree to which capacity fade is impacting the performance of implantable medical device 16, and allow judgments to be made as to if and when implantable medical device 16 should be explanted from patient 18 and be replaced.

In an alternative embodiment, the voltage output of rechargeable power source 24 is measured (812), and used to determine (814) a percentage of present charge level that is currently represented by the charge level. This percentage is then used to determine (816) the present charge level by multiplying the percentage by the total charge capacity. The present charge level is then outputted (818) to a user, in an embodiment as a gas gauge such as that used to display the total charge capacity compared with the total charge capacity at the initial time described above. In an embodiment, a time until recharge is estimated (820) based on past charge consumption, present settings, and anticipated patient 18 initiated therapy. The estimated time until recharge is then outputted (822) to a user via user output 51. Communication may be by telemetry, passive telemetry, radio frequency (RF), induction, ultrasound, audible sound, optics or other communication techniques. Time until recharge may be represented digitally or analog.

It is anticipated that the desirability of outputting various data, such as are described in the preceding paragraphs, may not be the same for every user. A patient 18 may have no interest in knowing total charge capacity or present charge level of their rechargeable power source 24, but would likely care to know a time until recharge. Thus, it is envisioned that only time until recharge would be displayed for patient 18. By contrast, a medical professional working with patient 18 may care to know total charge capacity, but not the other information. Thus, in an embodiment the above described data may be selectable by a user, and the outputting steps (810), (818), (822) may or may not occur, dependent on the preferences of the user.

Figure 9:
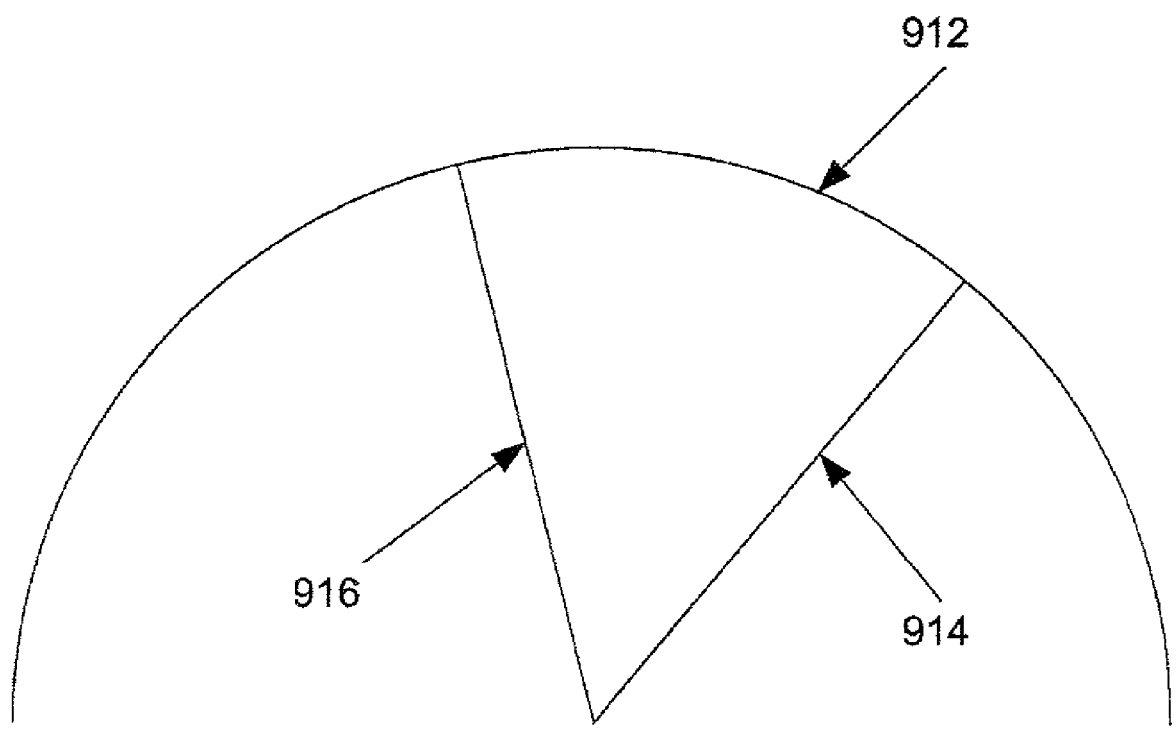
FIG. 9 shows an example of a graphical depiction of a total charge capacity at an initial time, total charge capacity and charge level of rechargeable power source.

FIG. 9 shows an example of a graphical depiction of a total charge capacity at the initial time, total charge capacity and present charge level of rechargeable power source 24 that may be displayed on user output 51. The area enclosed under arc 912 depicts the initial charge capacity of rechargeable power source 24. As a result of capacity fade, total charge capacity line 914 moves from right to left over arc 912, with the farther right total charge capacity line 914 is, the greater the total charge capacity and the less fade has impacted the capacity of rechargeable power source 24. Present charge level line 916 likewise moves from right to left across arc 912, but can, in no event, exceed total charge capacity, and thus present charge level line 916 can never exist to the right of total charge capacity line 914. In an alternative embodiment, two gas gauges may be displayed, one corresponding to total charge capacity relative to initial charge capacity, and another corresponding to present charge level relative to total charge capacity.

Figure 8:
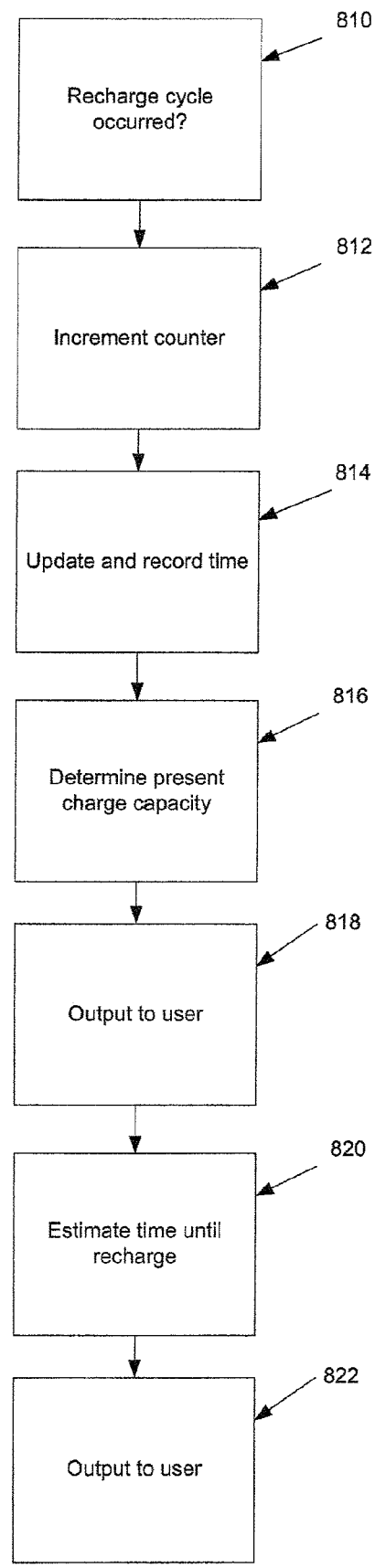
FIG. 8 is a flow chart of a method for estimating a time until recharge of a rechargeable power source.

An embodiment combining the results of the methods of FIGS. 5 and 8 is envisioned. In such an embodiment, the charge levels determined by each of the methods are averaged, with the average utilized to determine time remaining. Alternatively, one determined charge level may be weighted more heavily than another, dependent on the characteristics of the particular rechargeable power source 24 and implantable medical device 16 and any tendency for one method or the other to provide more consistently accurate results. As a further alternative embodiment, time until recharge may be determined using just one determined charge level, but the charge level determined from the other method may be compared against the utilized charge level to verify that the two determined charge levels are generally consistent with one another. If the two charge levels are inconsistent with one another then a new test may be prompted. If the two charge levels remain inconsistent then one or the other may be utilized, or the determination of time until recharge may be deemed a failure and a note to that effect displayed to a user, in an embodiment on charging unit 50.

Thus, embodiments of the method for estimating time before recharging a battery is required, and a system therefore are disclosed. One skilled in the art will appreciate that the present invention can be practiced with embodiments other than those disclosed. The disclosed embodiments are presented for purposes of illustration and not limitation, and the present invention is limited only by the claims that follow.

What is claimed is:
1. A system, comprising:
an implantable medical device having a rechargeable power source having a recharge interval until a time when recharge of said rechargeable power source is desired, said rechargeable power source having a voltage, a total charge capacity which changes over time and a charge level;
electronic componentry, operatively coupled to said implantable medical device, configured to:

record a cycle age by counting a number of recharges of said rechargeable power source indicative of a number of times said rechargeable power source has been recharged;

record a chronological age of said rechargeable power source;

determine said total charge capacity of said rechargeable power source at a first time by subtracting a charge capacity based, at least in part, on said cycle age of said rechargeable power source and a charge capacity based, at least in part, on said chronological age of said rechargeable power source from said total charge capacity at a second time, said second time being earlier than said first time;

measure a voltage of said rechargeable power source;

determine a state of charge as a function of said voltage;

determine a charge level of said rechargeable power source as a function of said total charge capacity at said first time and said state of charge; and determine said recharge interval as a function of said charge level and a programmed rate; and a user output, operatively coupled to said electrical componentry, configured to communicate said recharge interval to said user.

2. The system as in claim 1 wherein said cycle age is dependent, at least in part, on said number of recharges and a net charge passed through said rechargeable power source during each recharge of said rechargeable power source and said total charge capacity.

3. The system as in claim 1 wherein said cycle age is comprised, at least in part, of a linear function based on a number of charge cycles.

4. The system as in claim 1 wherein said chronological age is comprised, at least in part, of an exponential function based on time.

5. The system as in claim 1 wherein said user output is further configured to communicate a graphical depiction of said present charge capacity relative to said initial charge capacity to said user.

6. A system, comprising:
an implantable medical device having a rechargeable power source, said rechargeable power source having total charge capacity;
electronic componentry, operatively coupled to said implantable medical device, configured to:
record a cycle age by counting a number of recharges of said rechargeable power source indicative of a number of times said rechargeable power source has been recharged;
record a chronological age of said rechargeable power source;
determine said total charge capacity of said rechargeable power source at a first time by subtracting a charge capacity based on said cycle age of said rechargeable power source and a charge capacity based on said chronological age of said rechargeable power source from said total charge capacity at a second time, said second time being earlier than said first time; and
a user output, operatively coupled to said electronic componentry, configured to communicate said total charge capacity at said first time.

7. The system as in claim 6 wherein said user output is further configured to communicate a graphical depiction of said present charge capacity relative to said initial charge capacity to said user.

8. In an implantable medical device having a rechargeable power source, a method for determining a recharge interval until a time when recharge of said rechargeable power source is desired, said rechargeable power source having a total charge capacity and a charge level, comprising the steps of:
recording a cycle age by counting a number of recharges of said rechargeable power source indicative of a number of times said rechargeable power source has been recharged;
recording a chronological age of said rechargeable power source;
determining said total charge capacity of said rechargeable power source at a first time by subtracting a charge capacity based, at least in part, on said cycle age of said rechargeable power source and a charge capacity based, at least in part, on said chronological age of said rechargeable power source from said total charge capacity at a second time, said second time being earlier than said first time;
measuring a voltage of said rechargeable power source;
determining a portion of said present charge capacity as a function of said rechargeable voltage;
determining said charge level as a function of said total charge capacity at said first time and said portion of charge capacity remaining;
determining said recharge interval as a function of said total charge level at said first time and a programmed rate; and
outputting said recharge interval to a user.

9. The method of claim 8 further comprising the step of outputting said total charge capacity at said first time and said total charge capacity at said second time to said user.

10. The method as in claim 9 wherein said outputting step outputs a graphical depiction of said total charge capacity at said first time relative to said total charge capacity at said second time.

11. The method as in claim 8 wherein said charge capacity as a function of said number of recharges and said charge capacity as a function of said age of said rechargeable power source are determined using a model.

12. In an implantable medical device having a rechargeable power source, a method for determining a present charge capacity of said rechargeable power source, said rechargeable power source having a total charge capacity, comprising the steps of:
recording a cycle age by counting a number of recharges of said rechargeable power source indicative of a number of times said rechargeable power source has been recharged;
recording a chronological age of said rechargeable power source;
determining said total charge capacity of said rechargeable power source at a first time as a function of subtracting a charge capacity based on said cycle age of said rechargeable power source and a charge capacity based on said chronological age of said rechargeable power source from said total charge capacity at a second time, said second time being earlier than said first time;
outputting said total charge capacity at said first time and said total charge capacity at said second time to a user.

13. The method as in claim 12 wherein said outputting step outputs a graphical depiction of said total charge capacity at said first time relative to said initial charge capacity at said second time.

* * * * *